United States Patent [19]

Witiak et al.

[11] Patent Number: 5,298,526
[45] Date of Patent: Mar. 29, 1994

[54] OPTICALLY PURE STEREOGENICALLY LABILE 4-SUBSTITUTED-2-HYDROXYTETRONIC ACIDS AND PHARMACEUTICAL USE

[75] Inventors: Donald T. Witiak, Mt. Vernon, Ohio; Ashok K. Tehim, Montreal, Canada

[73] Assignee: The Ohio State University Research Foundation, Columbus, Ohio

[21] Appl. No.: 847,295

[22] Filed: Mar. 6, 1992

Related U.S. Application Data

[62] Division of Ser. No. 464,511, Jan. 12, 1990, Pat. No. 5,095,126.

[51] Int. Cl.$^5$ .................. A61K 31/365; C07D 307/62
[52] U.S. Cl. ..................... 514/473; 514/444; 514/474; 549/60; 549/315; 549/316
[58] Field of Search ................... 549/60, 315, 316; 514/444, 473, 474

[56] References Cited

FOREIGN PATENT DOCUMENTS 259707 3/1988 European Pat. Off. ............ 549/315
2114571 8/1983 United Kingdom ................ 549/315

OTHER PUBLICATIONS

R. E. Ireland et al., *J. Org. Chem.*, "An Approach to the Total Synthesis of Chlorothricolide," 44 (17), pp. 3041–3052 (1979).
G. Stork et al., *J. Am. Chem. Soc.*, "Iterative Butenolide Construction of Polypropionate Chains," 109, pp. 1565–1567 (1987).
Y. S. Rao, *Chemical Reviews*, "Recent Advances in Chemistry of Unsaturated Lactones" 76 (5) pp. 625–694 (1976).
D. T. Witiak et al., *J. Med. Chem.*, "Synthetic Aci-Reductones," 31 (7) pp. 625–694 (1976).
J. E. Wrobel, et al., *J. Org. Chem.*, "Total Synthesis of (−)-Vertinolide," 48 (21) pp. 3761–3764 (1983).
P. Booth, et al., *J. Chem. Soc. Perkin Trans I*, "Preparation of Acyltetronic Acids . . . " pp. 121–129 (1987).
B. Helferich et al., *Ber*, "Fine Neue Ascoibinsaure Synthese," 70, pp. 465–468 (1937).
S. Brandange et al., *J. Org. Chem.*, "Studies on Intramolecular Claisen Condensation," 49 pp. 928–931 (1984).
R. E. Ireland, *J. Org. Chem.*, "Approach to the Total Synthesis of Chlorothricolide," 51(5), pp. 635–648 (1986).
F. Corey et al., "Advanced Organic Chemistry," Part B, 2nd ed., Plenum Press, New York (1983).
J. March, "Advanced Organic Chemistry," ed., pp. 104–107 John Wiley & sons, New York (1985).
J. Bloomer et al., *J. Org. Chem.*, "Total Synthesis of α-Carboxymethyltetronic Acid" 39 113 (1974).
V. Komanna et al., *Lipids*, "Serum Lipoprotein and Apoprotein Concentrations in 4-(4-Chlorophenyl)-2-Hydroxytetronic Acid," 24(1) pp. 25–32 (1989).
G. Pattenden et al., *Fortschr. Chem. Orig. Naturst.*, "Natural 4-Ylidenebutenolides and 4-Ylidenetetronic Acids," 35 pp. 133–139 (1978).
Berdy, "Handbook of Antibiotic Compounds," CRC, Boco Raton Fla., 1980, vol. II, p. 415.
R. T. Witiak et al., *J. Med. Chem.*, "Hypocholesterolemic Acid Antiaggregatory Properties of 2-Hydroxytetronic Acid . . . " 25 (1), pp. 90–93 (1982).
J. Whitesell et al., *J. Org. Chem.*, "Resolution of Chiral Alcohols With Mandelic Acid," 48(20) pp. 3548–3551 (1983).
M. Gore, *J. Org. Chem.*, "Oxidation of Enolates by Dibenzyl Peroxydicarbonate to Carbonates . . . ," 0 51 (19) 3700–3704 (1986).
D. Evans et al., *Tetrahedron*, "The Asymmetric Synthesis of α-Amino and α-Hydrozino Acid Derivatives . . . " 44 (17) pp. 5525–5540 (1988).

*Primary Examiner*—Richard L. Raymond
*Attorney, Agent, or Firm*—Klauber & Jackson

[57] ABSTRACT

The present invention relates to a method for synthesis of optically pure stereogenically labile 4-substituted-2-hydroxytetronic acids from an asymmetric α-hydroxy ester. The chiron approach of the present invention utilizes a non-nucleophilic lithium amide base under kinetically controlled Claisen conditions to produce a 4-substituted-2-pheylmethoxy precursor to the 4-substituted-2-hydroxy tetronic acid. The invention further relates to the use of such optically pure compounds as potent inhibitors of platelet aggregation by working at the level of cyclooxygenase. The invention further relates to the pharmaceutical use of such compounds in the treatment of coronary artery diseases, especially in the treatment and/or prevention of atherosclerosis.

10 Claims, No Drawings

OPTICALLY PURE STEREOGENICALLY LABILE 4-SUBSTITUTED-2-HYDROXYTETRONIC ACIDS AND PHARMACEUTICAL USE

This invention was made with Government support under Grant No. RO1-HL12740-14A2 awarded by the U.S. Public Health Service National Heart, Lung and Blood Institute. The Government has certain rights in this invention.

This is a divisional of copending application Ser. No. 07/464,511 filed on Jan. 12, 1990 and now U.S. Pat. No. 5,095,126, issued Mar. 10, 1992.

The present invention relates to a method for the synthesis of optically pure stereogenically labile 4-substituted-2-hydroxytetronic acids from an asymmetric α-hydroxy ester. The chiron approach of the present invention utilizes lithium dicyclohexylamide or lithium hexamethydisilazide under kinetically controlled Claisen conditions to produce a 4-substituted-2-phenylmethoxy precursor to the 4-substituted-2-hydroxy tetronic acid. The invention further relates to the use of such optically pure compounds as potent inhibitors of platelet aggregation by working at the level of cyclooxygenase. The invention further relates to the pharmaceutical use of such compounds in the treatment of coronary artery diseases, especially in the treatment and/or prevention of atherosclerosis.

BACKGROUND OF THE INVENTION

The present invention relates generally to methods for the synthesis of optically pure 4-substituted-2-hydroxytetronic acid aci-reductone compounds.

The aci-reductone 4-(4-chlorophenyl)-2-hydroxytetronic acid compound (CHTA) of formula I

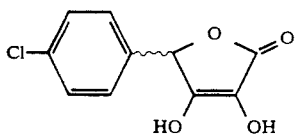

is known to exhibit antilipidemic and antiaggregatory properties which differ from those of the classical phenoxyacetic acids as has been disclosed in Witiak et al., *J. Med. Chem.*, 1988, 31, 1437-1445 and Kamanna et al., *Lipids*, 1989, 24, 25-32. Although, unsubstituted-, 2-alkyl- and 2-acyltetronic acids are frequently found in nature, Rao, *Chem. Revs.*, 1976, 76, 625-694 and Pattenden, *Fortschr. Chem. Org. Naturst.*, 1978, 35, 133-198; the 2-hydroxy substituted redox system, to our knowledge, is only found in vitamin C and the macrolide antibiotic chlorothricin, Berdy in *"Handbook of Antibiotic Compounds"*, CRC, Boca Raton, Fla., 1980, Vol. II, p. 415.

The antiaggregatory activities of 2-hydroxytetronic acid aci-reductone compound (CHTA) is of interest since blood platelets are involved in the genesis of atherosclerosis. 2-Hydroxytetronic acid aci-reductones inhibit collagen-induced human platelet aggregation and secretion of [$^{14}$C]-serotonin in a concentration-dependent manner at equivalent doses, as reported in Witiak et al., *J. Med. Chem.*, 1982, 25, 90-93. The CHTA compound inhibits platelet function by a similar mechanism, involving arachidonic acid release. Redox analogues such as 2-hydroxytetronic acid function as antioxidants in membranes or interfere with free radical processes involved in the biosynthetic elaboration of cyclic prostaglandin endoperoxides ($PGG_2$ and $PGH_2$) and subsequently thromboxane $A_2$ from arachidonic acid.

Synthesis of 4-substituted-2-hydroxytetronic acid compounds of the present invention is of formula II

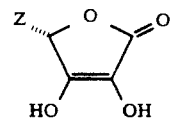

complicated by the sterochemical lability of the C-4 stereogenic center. The lability of this center in tetronic acids can be compared to the lability of the asymmetric center of mandelic acid; Whitesell et al., *J. Org. Chem.*, 1983, 48, 3548-3551 and Gore et al., *J. Org. Chem.*, 1986, 51, 3700-3704, and phenylglycine, Evans et al., *Tetrahedron*, 1988, 44, 5525-5540, Bodansky, *"Principles of Peptide Syn."*, Springer-Verlag, Berlin, N.Y., 1984, p. 160, which discloses that phenylglycine undergoes extensive racemization during peptide synthesis.

Older synthetic methods such as disclosed in Helferich et al., *Ber.*, 1937, 70, 465-468, involving benzoin and intermolecular Claisen condensations employed in the synthesis of L-ascorbic acid, produce racemic 4-aryl-2-hydroxytetronic acids. Various syntheses published for the naturally occurring chiral tetronic acids such as (—)-vertinolide (Wrobel et al., *J. Org. Chem.*, 1983, 48, 3761-3764); (S)-carlosic acid (Bloomer et al., *J. Org. Chem.*, 1974, 39, 113-125); chlorothricin (Ireland et al. *J. Org. Chem.*, 1986, 51, 635-648); related 2-acylated (Booth et al., *J. Chem. Soc. Perkin Trans I*, 1987, 121-129; or 2-unsubstituted (Brandange et al., *J. Org. Chem.*, 1984, 49, 927-928) tetronic acids, and chiral tetronic acid intermediates useful for the synthesis of the seco acid of erthronolide B (Stork et al., *J. Am. Chem. Soc.*, 1987, 109, 1564-1565), were not applicable for the synthesis of optically pure enantiomers of 4-aryl-2-hydroxytetronic acids. Some targets contain quaternary chiral centers not expected to undergo racemization during their preparation as disclosed in Wrobel et al., supra, and Ireland et al., supra.

Other syntheses are dependent upon intramolecular Claisen condensations facilitated by a second carbonyl function thereby affording 2-acyltetronic acids as disclosed in Bloomer et al., supra, and Booth, et al., supra. In some cases the 4-substituent at the chiral center is alkyl, as disclosed in Brandange et al., supra, and Stork, et al., supra, and therefore, racemization under reaction conditions employed is more easily prevented.

Thus, the literature contains no references to the preparation of optically pure stereogenically labile 4-substituted-2-hydroxytetronic acid compounds.

SUMMARY OF THE INVENTION

One aspect of the present invention relates to optically pure 4-substituted-2-hydroxytetronic acid compounds of the formula II

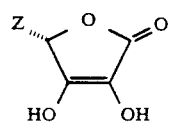

wherein Z is an aliphatic or aromatic substituent, such as a straight or branched alkyl or alkoxy-substituted alkyl group, a cycloaliphatic group, a halo-lower alkyl group, an aryl or aralkyl or substituted aryl or aralkyl group.

Another aspect of the present invention relates to a process for making optically pure 4-substituted-2-hydroxytetronic acid compounds of formula II as described above. The process comprises an intramolecular Claisen condensation synthesis involving the treatment of asymmetric α-hydroxy esters with phenylmethoxyacetyl chloride to give a phenylmethyoxyacetyl derivatuve which undergoes intramolecular Claisen condensation with a non-nucleophilic lithium amide base, such as, for example, lithium hexamethyl disilazide (LiHMDA) or lithium dicylohexylamide (LiN(Cy)$_2$) at temperatures in the range of about $-75°$ C. to about $-100°$ C. to yield 2-phenylmethoxytetronic acid which is thereafter deprotected under transfer hydrogenation conditions to yield the compound of formula II.

In a composition aspect, the present invention encompasses novel pharmaceutical compositions comprising a compound of the formula II, together with a physiologically acceptable carrier or excipient, in an amount sufficient to have antilipidemic or antiaggregatory activities in an animal or patient. The compounds of the present invention are useful in the treatment or prevention of atherosclerotic disorders.

DESCRIPTION OF THE INVENTION

The invention provides optically pure compounds of the general formula II

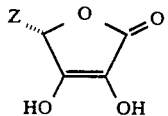

wherein Z is selected from the group comprising $C_1-C_8$ straight or $C_1-C_8$ branched alkyl or alkoxy-substituted alkyl group, $C_3-C_8$ cycloaliphatic group, a halo-$C_1-C_8$ alkyl group, aryl or aralkyl group, or substituted aryl or aralkyl group.

As used herein, the term "alkyl" means straight- or branched-chain saturated aliphatic hydrocarbon groups preferably containing 1-8 carbon atoms. Representative of such groups are methyl, ethyl, isopropyl, butyl, pentyl, hexyl and the like.

The term "cycloaliphatic" means a lower alkyl hydrocarbon group which is closed to form a ring structure. Preferred cycloaliphatic groups are saturated lower alkyl hydrocarbon ring structures containing from 3-6 carbon atoms. Especially-preferred are saturated groups containing 4-6 carbon atoms.

The term "alkoxy" means a lower alkyl group attached to the remainder of the molecule by oxygen. Examples of alkoxy are methoxy, ethoxy, propoxy, isopropoxy and the like.

The term "aryl" means an organic, aromatic radical derived by the removal of one atom (e.g., phenyl) which can be substituted or unsubstituted by one or more lower alkyl groups (e.g., tolyl).

The term "aralkyl" means a group in which an alkyl atom is substituted by an aryl group wherein aryl and alkyl are as defined above. Examples of aralkyl are benzyl and phenethyl.

The term "substituted aryl or aralkyl" means araryl or aralkyl group substituted by a halogen, lower alkyl, alkoxy, aromatic or heteroaromatic group. Examples include: substituted phenyls (ortho, meta or para) i.e., disubstituted 2,3-dichlorophenyl-, 2,4-dichlorophenyl-; and thiophene.

The invention also provides for compositions comprising the optically pure compounds of the general formula II above, and the physiologically acceptable salts thereof (such as, for example, Na$^+$, K$^+$, NH$_4^+$). The invention also provides processes for the preparation of the optically pure compounds of the general formula II above. The invention provides, in particular, compounds and processes for their preparation, of the general formula II above wherein Z is an alkyl group (for example methyl) or biphenyl group.

The compounds of the invention have antilipidemic and antiaggregatory activity and are useful in the treatment or prevention of atherosclerotic disorders. The invention accordingly further provides optically pure compounds of the general formula II and their physiologically acceptable salts for use in the therapy or prophylaxis of atherosclerotic disorders.

The compounds according to the invention may be formulated in a conventional manner, optionally together with one or more other active ingredients, for administration by any convenient route for example for oral, intravenous or intramuscular administration.

Thus, according to another aspect, the invention provides a pharmaceutical composition comprising a compound of general formula II and/or a physiologically acceptable salt thereof together with a physiologically acceptable carrier or excipient.

For oral administration, the pharmaceutical composition may take the form of, for example, tablets, capsules, powders, solutions, syrups or suspensions prepared by conventional means with physiologically acceptable excipients.

The compounds may be formulated for intravenous or intramuscular administration in dry form for reconstitution before use, or as a sterile solution or suspension.

A proposed daily dose based on similar pharmacokinetic parameters to CHTA for administration to man is 10 to 25 to mg/kg, for example, 1 gm daily to 70 kg., which may be conveniently administered in 1 to 3 doses per day. The optically pure compounds of the present invention are less toxic than the CHTA compounds; accordingly the dosage administered to the patient can reflect such decreased toxicity. The precise dose administered will of course depend on the age and condition of the patient.

In the following examples the group Z is as previously defined for general formula II above, except where otherwise indicated.

According to a first example, a compound of formula II may be prepared as follows:

The intramolecular Claisen condensation involving use of a non-nucleophilic sterically hindered base is used as the approach for the synthesis of optically pure 4-substituted-2-hydroxytetronic acids of known absolute configuration of general formula II from accessible asymmetric α-hydroxy esters of the formula III, wherein R can be a lower alkyl, for example Me or Et.

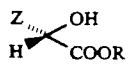

Such a Claisen condensation is a particularly facile intramolecular process suitable for the construction of tetronic acids via C2–C3 bond connection. Thus, a phenylmethoxyacetyl derivative of the formula IV, wherein Bn is a benzyl group

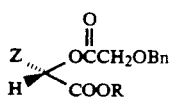

can be prepared from the ester of formula III and phenylmethoxyacetyl chloride. The compound of formula IV then under goes intramolecular Claisen condensation with either lithium hexamethyldisilazide (LiHMDA) or lithium dicyclohexylamide (LiNCCy)₂ at temperatures in the range of about −75° C. to about −100° C. to afford the 2-phenylmethoxytetronic acid compound of the formula V

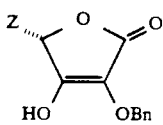

without detectable epimerization.

The enantiomeric purity of the protected tetronic acid (S)-(+) wherein Z=Me (>98% e.e.) was determined using high resolution NMR (500 MHz) analysis of the chiral amine [(S)-methylbenzylamine] salt compared to the salt derived from the racemic compound of the formula V. For the (S)-(+) formula V salt wherein Z=Me a single quartet (J=7.1 Hz) was observed at δ4.88 for the proton bonded to the chiral center. Two overlapping quartets were observed for the salt of the racemic compound. Transfer hydrogenation as described in Ananthanamaiah et al., *J. Chem. Soc., Perkin Trans. I*, 1977, 490–491, produced the target aci-reductone compound of formula II, wherein Z=Me in 79% yield.

According to a second example, compounds of general formula II may be prepared as follows: The protected ester of formula IV wherein Z=Ph and R=Me was generated from methyl (S)-(+)-mandelate of formula III wherein Z=Ph and R=Me in 84% yield. Use of 2.1 eq. of LiN(Cy)₂ (−78° C., 10 min) provided 2-phenylmethoxytetronic acid of formula V wherein Z=Ph (35% yield, 88–92% e.e.) but at −100° C., 10 min. the e.e. was>98% (250 MHz NMR).

Debenzylation under transfer hydrogenation conditions afforded enantiomerically pure target formula II wherein Z=Ph, (S)- in 40% yield. The enantiomeric excess was determined by observing the 4-H proton resonance signal of optically pure (S)-formula V and deprotected species (S)-formula II as their (S)-methylbenzylamine salts.

The successful use of relatively unexplored LiN(Cy)₂ to provide 2-hydroxytetronic acid redox compounds of high enantiomeric purity is unprecedented. Furthermore, these intramolecular Claisen condensations are applicable for construction of a wide range of optically pure 4-substituted-2-hydroxytetronic acids of known absolute configuration. Such a chiron approach becomes all the more practical since methodologies for the preparation of α-hydroxy acid precursors of known absolute configuration are available. Optically pure, but commercially unavailable α-hydroxy ester precursors, are available using Evan's chiral oxazolidinone auxiliaries, Evans et al., *J. Am. Chem. Soc.*, 1985, 107, 4346–4348. For example, we have prepared methyl (S)-α-hydroxy-α biphenylacetate in high optical yield (94% e.e) from 4-biphenylacetyl chloride, Logemann, W., *Hoppe-Seylers Z. Physiol. Chem.*, 1952, 290, 61–66, and (S)-4-isopropyloxazolidin-2-one. Treatment of the resulting oxazolidinone carboximide (76%) with LiHMDA and dibenzylperoxy dicarbonate yielded the intermediate carbonate as a single diastereomer (71%, d.e.>98%). Lithium hydroperoxide, Evans et al., *Tetrahedron Lett.*, 1987, 28, 6141–6144, hydrolysis afforded the protected hydroxy acid (78%). Removal of the chiral auxilliary with Mg(OCH₃)₂, Evans et al., *J. Am. Chem. Soc.*, supra., (0.02M; 1.1 eq) at −15° C. to −20° C. followed by deprotection via transfer hydrogenation yielded partially racemized α-hydroxy ester [(35% e.e., [α]²²_D+49.1° (c 1.00, MeOH)] in 61% overall yield from the oxazolidinone carboximide. Transfer hydrogenation generated the (S)-α-hydroxyacetic acid (83%), and esterification (diazomethane) yielded the methyl acetate (91%), the enantiomeric purity of which was determined by conversion to the α-methoxy-α-trifluoromethyl phenyl acetic acid (MPTA) ester with (+)-MPTA-Cl, Dale et al., *J. Org. Chem.*, 1969, 34, 2543–2549, and observing the benzylic proton signal [¹H NMR (CDCl₃), 250 MHZ] at δ6.15 (s, 1H) in comparison to the ester derived from racemic hydroxy ester. The racemic methyl α-hydroxyacetate, mp 104°–105° C., was prepared by CH₂N₂ esterification of the racemic acid which was synthesized as follows: in situ cyanosilylation, Rasmussen et al., *Organic Syntheses*, 1984, 62, 196–201, [Me₃SiCl, KCN, Zn(CN)₂] of 4-biphenylcarboxaldehyde furnished trimethylsilyl cyanohydrin ether which was hydrolysed with HCl, Grunewald et al., *Tetrahedron Lett.*, 1980, 21, 1219–1220, to the hydroxy amide (m.p. 226°–227° C.) and finally to racemic α-hydroxy acid (m.p. 201°–202° C., Lit. mp 201°–203° C.) Blicke et al., *J. Am. chem. Soc.*, 1943, 65, 1725–1728, with KOH/MeOH in 56% overall yield.

The following examples illustrate the present invention. Melting points were determined in open capillaries and are uncorrected.

EXAMPLE 1

Ethyl (S)-(−)-2-(Phenylmethoxyacetoxy) propanoate. To a stirred solution (0° C.) of 1.0 g (8.47 mmol) of ethyl (S)-lactate in 8.0 mL of dry CH₂Cl₂ containing 2.0 mL (12.7 mmol) of phenylmethoxyacetyl chloride was added 1.0 mL (12.4 mmol) of dry pyridine. The resulting mixture was stirred for 0.5 h, warmed to room temperature and stirred for an additional 1 h. The mixture was poured into ice cold H₂O (25 mL) containing 10 mL of CH₂Cl₂. After standing overnight in order to ensure complete hydrolysis of the acid chloride, the organic layer was separated and washed with H₂O (2×15 mL), 10% aqueous HCl (2×10 mL), saturated NaHCO₃ solution (2×10 mL), brine (2×10 mL), dried (Na₂SO₄), and concentrated in vacuo. The residual oil was purified over silica gel-CH₂Cl₂, and distilled (Vigreux column) affording 1.93 g (86%) of colorless oil bp 150°–151° C. (1.25 torr). [α]²²_D−35.3° (c 1.10, MeOH); IRγ_max^neat 2980, 1750, 1450, and 1370 cm⁻¹; ¹H NMR (CDCl$_3$, 250 MHz) δ1.28 (t, 3H, J=7.1 Hz), 1.51 (d, 3H, J=7.1 Hz), 4.20 (s, 2H), 4.24 (q, 2H, J=7.1 Hz), 4.66 (s, 2H), 5.18 (q, 1H, J=7.1 Hz), 7.28–7.40 (m, 5H). Anal. calcd for C$_{14}$H$_{18}$O$_5$:C, 63.14; H, 6.81. Found: C, 62.86; H, 6.62.

EXAMPLE 2

(S)-(+)-4-Hydroxy-5-methyl-3-(phenylmethoxy)-2(5H)-furanone. To a stirred solution (−78° C.) of 3.95 mmol of LiHMDA in 20.0 mL of dry tetrahydrofuran (THF) (2.47 mL of 1.6M n-butyllithium in hexane and 0.83 mL of hexamethyldisilazane) under an argon atmosphere was added dropwise a solution of 0.5 g (1.88 mmol) of ethyl (S)-(−)-2-(phenylmethoxyacetoxy) propanoate in 5.0 mL of THF. The resulting mixture was allowed to stir at −78° C. for 1 h. Following quenching with 10% HCl solution (10 mL), Et$_2$O was added and the mixture was warmed to room temperature. The organic layer was removed and washed with brine (2×10 mL), dried (Na$_2$SO$_4$) and concentrated in vacuo. Crystallization of the residue from Et$_2$O/petroleum ether afforded 0.34 g (82%) of colorless prisms mp 114°–115° C. [α]$^{22}_D$+20° (c 1.00, MeOH); IRγ$_{max}^{neat}$ 2990, 2710, 1740, 1660, 1500, 1455, 1440, 1400, 1350 cm$^{-1}$; $^1$H NMR (CD$_3$COCD$_3$, 250 MHz) δ1.35 (d, 3H, J=6.6 Hz), 4.75 (q, 1H, J=6.6 Hz), 5.03 (s, 2H), 7.28–7.43 (m, 5H). Anal. calcd for C$_{12}$H$_{12}$O$_4$: C, 65.44; H, 5.49. Found: C, 65.57; H, 5.58.

EXAMPLE 3

The (S)-(−)α-methylbenzylamine salt of the compound of Example 2. (S)-(−)-methylbenzyl-amine (0.03 mL, 0.23 mmol) was added dropwise to 0.05 g (0.03 mmol) of (S)-(+) compound of Example 2 dissolved in MeOH (1 mL). Concentration in vacuo afforded a residue which was subjected to $^1$H NMR analysis (270 and 500 MHz).

EXAMPLE 4

(S)-(+)-3,4-Dihydroxy-5-methyl-2(5H)-furanone. To a solution of the compound (S)-(+) of Example 2 (0.05 g, 0.23 mmol) in EtOH (10 mL) were added 10% palladium on charcoal (Pd/C) (0.05 g) and cyclohexene (0.58 mL, 5.68 mmol). The mixture was refluxed for 1 h under argon, filtered, and concentrated in vacuo. Recrystallization of the residue from acetone/hexane afforded 0.024 g (79%) of colorless prisms mp 178°–179° C. (lit. mp for racemic 3,4-dihydroxy-5-methyl-2(5H)-furanone 174.5°–176.5° C.). [α]$^{22}_D$+4.7° (c 1.00, MeOH); IRγ$_{max}^{neat}$ 3350, 3040, 1760, 1640, 1440, 1340, 1290, 1210, 1160 cm$^{-1}$; $^1$H NMR (CD$_3$COCD$_3$, 250 MHz) δ1.38 (d, 3H, J=6.6 Hz), 4.74 (q, 1H, J=6.6 Hz). Anal. calcd for C$_5$H$_6$O$_4$: C, 46.16; H, 4.65. Found: C, 46.02; H, 4.69.

EXAMPLE 5

Methyl (S)-(+)-phenyl-2-(phenylmethoxyacetoxy)ethanote. To a stirred solution (0° C.) of 1.0 g (6.02 mmol) of methyl (S)-(+)-mandelate in 15.0 mL of dry CH$_2$Cl$_2$ containing 1.4 mL (9.03 mmol) of phenylmethoxy-acetyl chloride was added 0.7 mL (8.65 mmol) of dry pyridine. The resulting mixture was for 1 h, warmed to room temperature and stirred for an additional 3 h. The mixture was poured into ice cold H$_2$O (30 mL) and CH$_2$Cl$_2$ (10 mL). After standing overnight to ensure complete hydrolysis of acid chloride, the organic layer was separated and washed with H$_2$O (2×15 mL), 10% aqueous HCl (2×10 mL), saturated NaHCO$_3$ solution (2×10 mL), brine (2×10 mL), dried (Na$_2$SO$_4$), and concentrated in vacuo. The residual oil was purified over silica gel-petroleum ether/Et$_2$O (90:10) affording 1.5 g (84%) of colorless needles mp 50°–51° C. [α]$^{22}_D$+97.0° (c 1.00, CHCl$_3$); IRγ$_{max}^{neat}$ 2890, 1750, 1440, 1430, 1390, 1340, 1200, 1125 cm$^{-1}$; $^1$H NMR (CDCl$_3$, 250 MHz) δ3.73 (s, 3H), 4.23 (d, 1H, J=16.8 Hz), 4.29 (d, 1H, J=16.8 Hz), 4.67 (s, 2H), 6.04 (s, 1H), 7.29–7.49 (m, 10H). Anal. calcd for C$_{18}$H$_{18}$O$_5$: C, 68.78; H, 5.77. Found: C, 68.86; H, 5.84.

EXAMPLE 6

(S)-(+)-4-Hydroxy-5-phenyl-3-(phenylmethoxy)-2(5H)-furanone. To a stirred solution (−100° C.) of 2.67 mmol of LiN(Cy)$_2$ in 20.0 mL of dry THF (1.67 mL of 1.6M n-butyl lithium in hexane and 0.53 mL of dicyclohexylamine) under an argon atmosphere was added dropwise a solution of 0.4 g (1.27 mmol) of the (S)-(+) compound of Example 5 in 2.5 mL of THF. The mixture was stirred at −100° C. for 10 min. and quenched with a cooled solution of 10% aqueous HCl (5 mL). Et$_2$O (15 mL) was added, the mixture warmed to room temperature, and the organic layer separated and washed with brine (5 mL) and extracted with 10% NaHCO$_3$ solution (2×5 mL). The aqueous extract was acidified (cold 10% aqueous HCl) and extracted with Et$_2$O (2×10 mL). The Et$_2$O layer was washed with brine (2×4 mL), dried (Na$_2$SO$_4$) and concentrated in vacuo. Recrystallization of the residue from hexane/Et$_2$O afforded 0.11 g (30%) of colorless prisms mp 124°–125° C. [α]$^{22}_D$+39.7° (c 1.00, MeOH); IR γ$_{max}^{neat}$ 2920, 2680, 1735, 1650, 1390, 1340, 1140; $^1$H NMR (CDCl$_3$, 250 MHz) δ5.14 (d, 1H, J=11.4 Hz), 5.18 (d, 1H, J=11.4 Hz), 5.51 (s, 1H), 7.08–7.12 (m, 2H), 7.26–7.43 (m, 8H). Anal. calcd for C$_{17}$H$_{14}$O$_4$:C, 72.33; H, 5.00. Found: C, 72.54; H, 5.08.

EXAMPLE 7

(S)-(+)-3,4-dihydroxy-5-phenyl-2(5H)-furanone. To a solution of the (S)-(+) compound of Example 6 (0.04 g, 0.14 mmol) in EtOH (5 mL) were added 10% Pd/C (0.04 g) and cyclohexene (0.36 mL, 3.56 mmol). The mixture was refluxed for 1 h under argon, filtered and concentrated in vacuo. Recrystallization of the residue from acetone/hexane afforded 0.01 g (40%) of colorless needles mp 142°–143° C. (lit mp for racemic compound 150.5°–152° C. dec. Dahn et al., Helv. Chim. Acta., 1954, 37, 1318–1327.). [α]$^{22}_D$+109.4° (c 0.80, MeOH); IR γ$_{max}^{neat}$ 3300, 1740, 1640 cm$^{-1}$; $^1$H NMR (CDCl$_3$+d$_6$-DMSO, 250 MHz) δ4.98 (s, 1H), 7.23–7.41 (m, 5H). Anal. calcd for C$_{10}$H$_8$O$_4$: C, 62.50, H, 4.20. Found: C, 62.69; H, 4.25.

We claim:

1. An optically pure compound, 3,4-dihydroxy-5-substituted-2(5H)-furanone of the formula I:

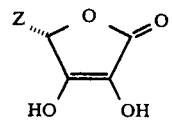

wherein Z is selected from the group consisting of C$_1$–C$_8$ straight or branched alkyl or alkoxy-substituted alkyl group, C$_3$–C$_8$ cycloalphatic group, a halo C$_1$–C$_8$ alkyl group, aryl or aralkyl group, and an aryl or aralkyl group substituted by one or more halogen, lower alkyl, alkoxy, or phenyl substituents, or a physiologically acceptable salt thereof.

2. The optically pure compound of claim 1, wherein Z is a $C_1$–$C_8$ straight or branched alkyl group.

3. An optically pure compound of claim 2, wherein Z is a methyl group.

4. The optically pure compound of claim 1, wherein Z is an aryl group.

5. An optically pure compound of claim 4 wherein Z is a phenyl group.

6. A pharmaceutical composition comprising an effective amount of a compound selected from the group consisting of an optically pure compound, 3,4-dihydroxy-5-substituted-2(H)-furanone of formula I:

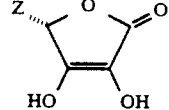

wherein Z is selected from the group consisting of $C_1$–$C_8$ straight or branched alkyl or alkoxy-substituted alkyl group, $C_3$–$C_8$ cycloalphatic group, a halo $C_1$–$C_8$ alkyl group, aryl or aralkyl group, and an aryl or aralkyl group substituted by one or more halogen, lower alkyl, alkoxy, or phenyl substituents, or a physiologically acceptable salt thereof together with a physiologically acceptable carrier or excipient.

7. The pharmaceutical composition of claim 6, wherein Z is a $C_1$–$C_8$ straight or branched alkyl group.

8. The pharmaceutical composition of claim 6, wherein Z is a methyl group.

9. The pharmaceutical composition of claim 6, wherein Z is an aryl group.

10. The pharmaceutical composition of claim 9 wherein Z is a phenyl group.

* * * * *